United States Patent
Falk

(10) Patent No.: US 11,020,611 B1
(45) Date of Patent: Jun. 1, 2021

(54) INTEGRATED PHOTOTHERAPEUTIC METER IN FIBEROPTIC PHOTOTHERAPY

(71) Applicant: GE Precision Healthcare LLC, Wauwatosa, WI (US)

(72) Inventor: Steven M. Falk, Baltimore, MD (US)

(73) Assignee: GE Precision Healthcare LLC, Wauwatosa, WI (US)

(*) Notice: Subject to any disclaimer, the term of this patent is extended or adjusted under 35 U.S.C. 154(b) by 0 days.

(21) Appl. No.: 16/736,239

(22) Filed: Jan. 7, 2020

(51) Int. Cl.
*A61N 5/06* (2006.01)

(52) U.S. Cl.
CPC ...... *A61N 5/0621* (2013.01); *A61N 2005/063* (2013.01); *A61N 2005/0628* (2013.01); *A61N 2005/0632* (2013.01); *A61N 2005/0666* (2013.01)

(58) Field of Classification Search
CPC .......... A61N 5/0621; A61N 2005/0628; A61N 2005/063; A61N 2005/0622; A61N 2005/0666
See application file for complete search history.

(56) References Cited

U.S. PATENT DOCUMENTS

| | | | | |
|---|---|---|---|---|
| 5,339,223 | A * | 8/1994 | Kremenchugsky | A61N 5/0621 362/276 |
| 6,596,016 | B1 * | 7/2003 | Vreman | A61N 5/0621 128/903 |
| 2002/0138120 | A1 * | 9/2002 | Whitehurst | A61N 5/062 607/88 |
| 2014/0012354 | A1 * | 1/2014 | Matsubara | A61N 5/0621 607/93 |
| 2018/0133505 | A1 * | 5/2018 | Verver-Klompenhouwer | A61B 5/207 |
| 2019/0099616 | A1 | 4/2019 | Sethumadhavan et al. | |
| 2019/0224496 | A1 * | 7/2019 | Van Abeelen | A61B 5/14551 |

* cited by examiner

*Primary Examiner* — Walter L Lindsay, Jr.
*Assistant Examiner* — Milton Gonzalez
(74) *Attorney, Agent, or Firm* — Andrus Intellectual Property Law, LLP

(57) ABSTRACT

A phototherapy device includes a blanket for use in phototherapy treatment that integrates a light emitting panel and a light receiver such that the amount of treatment light delivered to the infant patient can be determined. The light emitting panel includes a plurality of woven optical fibers that each receive treatment light from a light source. A second plurality of receiving optical fibers are woven into the light emitting panel. A reflective element is positioned on the light emitting panel to reflect a portion of the therapy light into the light receiver. A light detector determines the intensity of the treatment light being delivered to the infant patient during phototherapy.

17 Claims, 3 Drawing Sheets

INTEGRATED PHOTOTHERAPEUTIC METER IN FIBEROPTIC PHOTOTHERAPY

BACKGROUND

The present disclosure relates to devices and methods used in the treatment of neonatal hyperbilirubinemia (infant jaundice). More specifically the present disclosure relates to a phototherapy blanket that includes an integrated light receiver and light detector that is capable of monitoring the therapy light delivered to the infant patient.

Livers of some newborns are not mature enough to filter out bilirubin. Excessive bilirubin accumulated in the blood results in hyperbilirubinemia (jaundice), which may cause brain damage and even death. Phototherapy is an effective method for treating neonatal hyperbilirubinemia where bilirubin molecules absorb light in the blue spectra (e.g., wavelength of 425-475 nm) and convert into water soluble isomers which are then excreted by the body. For phototherapy treatment to be effective, the blue light needs to penetrate the skin to reach bilirubin molecules in the blood. However, a portion of the blue light is absorbed by the skin, resulting in reduced phototherapy efficiency. Improvement of phototherapy efficiency is generally desired.

SUMMARY

In one embodiment, the present disclosure provides a system for use in phototherapy treatment of a patient. The system includes a light source that is configured to generate treatment light used in the phototherapy treatment. A blanket is coupled to the light source to receive the treatment light and deliver the treatment light to the patient when the patient is received on the blanket. A light receiver is integrated into the blanket and is operable to receive a portion of the treatment light delivered to the patient. In one embodiment, the light receiver is a plurality of receiving optical fibers. The system further includes a light detector coupled to the light receiver. The light detector is operable to determine an amount of treatment light delivered to the patient by the blanket.

In another embodiment, a blanket for use in phototherapy treatment of a patient is provided. The blanket of the exemplary embodiment includes a light emitting panel configured to receive treatment light from the light source and deliver the treatment light to the patient when the patient is placed on the blanket. The blanket further includes a light receiver integrated into the blanket and operable to receive a portion of the treatment light delivered to the patient. The treatment light received by the light receiver can be monitored to determine the level of operation of the light emitting panel of the blanket.

In yet another embodiment, the present disclosure provides a method of providing phototherapy treatment to a patient. The method includes providing a blanket including a light emitting panel and a light receiver. A treatment light is delivered to the light emitting panel of the blanket such that the light emitting panel emits the treatment light to the patient when the patient is positioned on the blanket. A portion of the emitted treatment light is received by a light receiver that is integrated into the blanket. The received portion of the emitted treatment light is directed to a light detector. The light detector operates to determine the amount of treatment light emitted by the light emitting panel.

Figure 1:
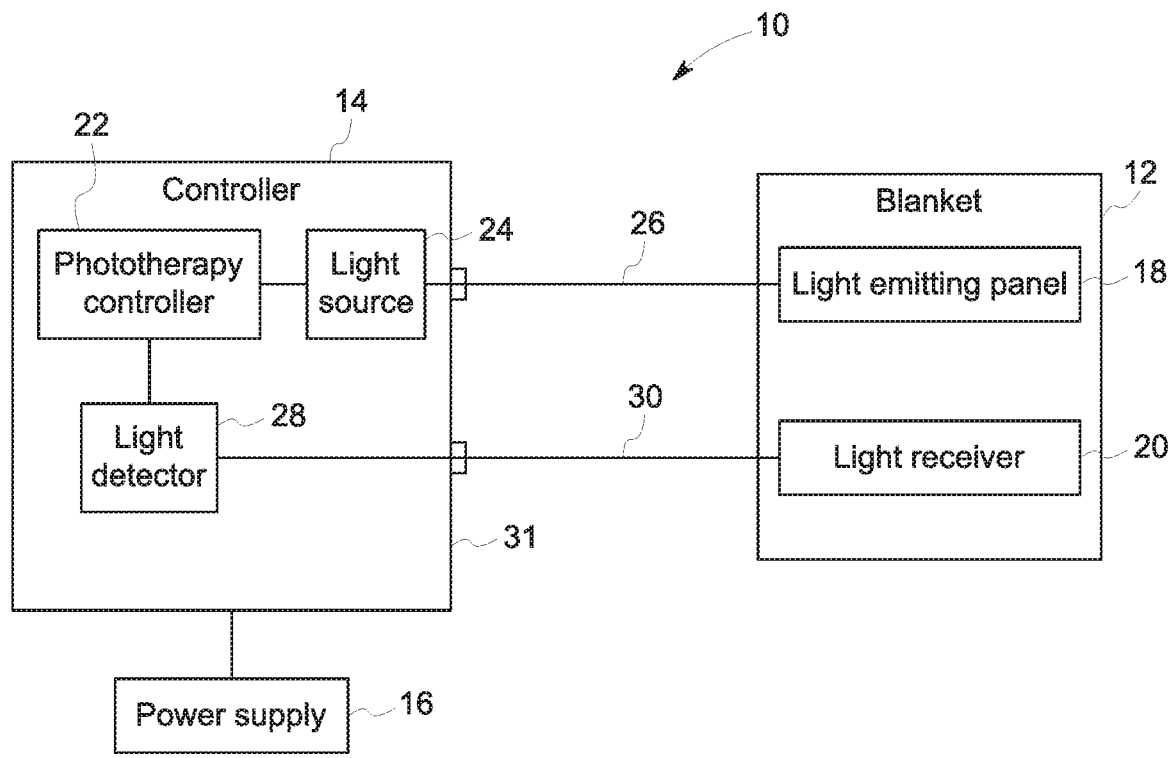
FIG. 1 is block diagram view of an exemplary embodiment of the phototherapy device constructed in accordance with the present disclosure.

The drawings illustrate specific aspects of the described components, systems and methods for providing phototherapy treatment. Together with the following description, the drawings demonstrate and explain the principles of the structures, methods, and principles described herein. In the drawings, the thickness and size of components may be exaggerated or otherwise modified for clarity. Well-known structures, materials, or operations are not shown or described in detail to avoid obscuring aspects of the described components, systems and methods.

DETAILED DISCLOSURE

One or more specific embodiments of the present disclosure are described below in order to provide a thorough understanding. These described embodiments are only examples of the systems and methods for providing phototherapy treatment. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features Referring to the figures generally, the present disclosure is to provide devices and methods for phototherapy treatment with improved efficiency. An exemplary device includes a blanket that includes a phototherapy element for delivering phototherapy to an infant placed on, or at least partially surrounded by, the blanket. Blue light, when penetrating the skin to reach bilirubin molecules in the blood for phototherapy, is partially absorbed by the skin. During use, it is necessary to determine the amount and intensity of treatment light delivered to the infant patient by the blanket.

In addition, a blanket integrating the phototherapy element enables developmental care of the infant. Kangaroo care, involving skin to skin contact between the infant and the mother, is an important component of developmental care. The blanket as disclosed herein is easily portable—the infant may be carried within the blanket. The infant may be comforted and/or transported by a caregiver while the phototherapy element is in use. Therefore, the developmental/Kangaroo care can be delivered without stopping the phototherapy.

When utilizing a blanket integrating the phototherapy element, a separate light meter is often utilized, separate from the phototherapy blanket, to measure the amount of treatment light that is being delivered by the phototherapy element of the blanket. The inventor recognized the problem that a separate light meter is often unavailable, cannot be found and can be misused. When recognizing this problem, the inventor of the present disclosure developed the subject matter of the present disclosure to integrate a light meter into the blanket including the phototherapy element.

FIG. 1 is a block diagram of a phototherapy device 10 constructed in accordance with one exemplary embodiment of the present disclosure. As illustrated in FIG. 1, the phototherapy device 10 includes a blanket 12, a controller 14 and a power supply 16. The blanket 12 is designed to be used in close proximity to an infant patient to deliver phototherapy with a light emitting panel 18 that is designed to deliver treatment light to the infant patient. In the embodiment shown in FIG. 1, the blanket 12 further includes a light receiver 20 that is integrated into the blanket and is designed to detect the amount of light being given off by the light emitting panel 18. Although not shown in FIG. 1, it is contemplated that the blanket 12 could also include some type of heating element, such as is disclosed in U.S. Patent Publication No. 2019/0099616. The blanket 12 is designed in the exemplary embodiment such that it can be wrapped around the infant patient to at least partially surround the infant patient. The infant patient can also be carried in the blanket 12 for Kangaroo care without stopping phototherapy. The details of the structure of the blanket 12 are discussed in further detail below with reference to FIGS. 2-3.

The controller 14 in the exemplary embodiment includes a phototherapy controller 22 that is configured to control the operation of a light source 24 that provides therapy light to the light emitting panel 18 through a bundle of fiber optic fibers that create a first cable 26. The controller 14 further includes a light detector 28 that is shown connected to the light receiver 20 integrated into the blanket 12 through a second series of bundled fiber optic fibers that create a second cable 30. The light detector 28 is operable to detect and determine the amount of light received at the light receiver 20 in the blanket 12, as will be discussed in much greater detail below.

The power supply 16 is configured to supply power to the various components of the controller 14. In some embodiments, the power supply 16 includes a direct current (DC) power supply, such as a battery pack, so that the phototherapy device 10 can be highly portable. In some embodiments, the power supply 16 includes an alternating current (AC) power supply, such as an AC-DC adapter that can be plugged into an AC wall outlet. In some embodiments, the power supply 16 includes both DC power supply and AC power supply. In such embodiment, when the infant is in bed, the AC power supply is plugged into the AC wall outlet and the DC power supply (e.g., rechargeable battery) can be charged and when the infant is moved around, the AC power supply is unplugged and the DC power supply is put in use. In some embodiments, the controller 14 and the power supply 16 are enclosed in a housing 31 (e.g., a box) outside of the blanket 12.

Figure 2:
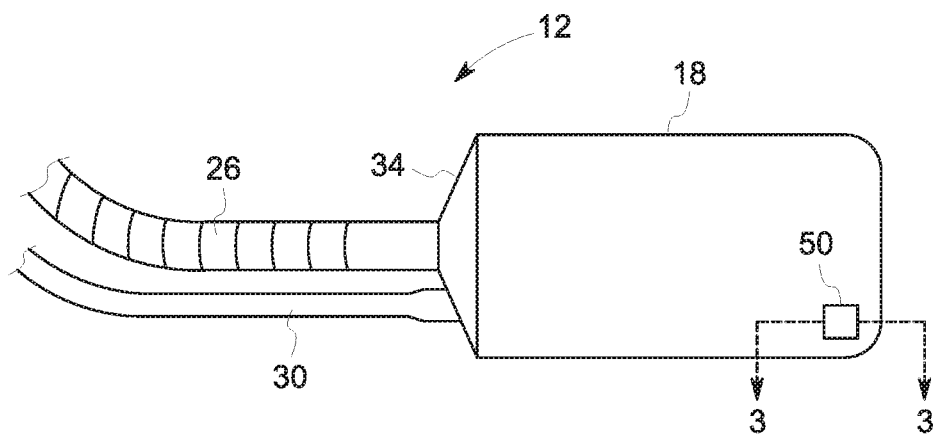
FIG. 2 is a schematic plan view of a blanket that can be used in the phototherapy device of FIG. 1.

FIG. 2 illustrates a first embodiment of the blanket 12 constructed in accordance with one exemplary embodiment of the present disclosure. As illustrated in FIG. 2, the blanket 12 includes the light emitting panel 18 that is connected to the light source of the controller 14 through the first fiber optic cable bundle 26. In the embodiment shown, the light emitting panel 18 is made from one or more layers of optical fibers woven into a sheet or mat. In use, an infant is placed on the light emitting panel 18 to receive phototherapy. The optical fibers at one end 34 of the light emitting panel 18 are brought together and bundled to form the first fiber optic cable 26 (e.g. ribbon cable or round cable). The first fiber optic cable 26 can transmit light from the remote light source 24 that is located within the housing 31 with the phototherapy controller 22 for providing the treatment light to the infant. The woven fiber light emitting panel 18 is formed in a manner such that the blanket 12 is flexible and can be wrapped around the infant patient as desired.

Figure 3:
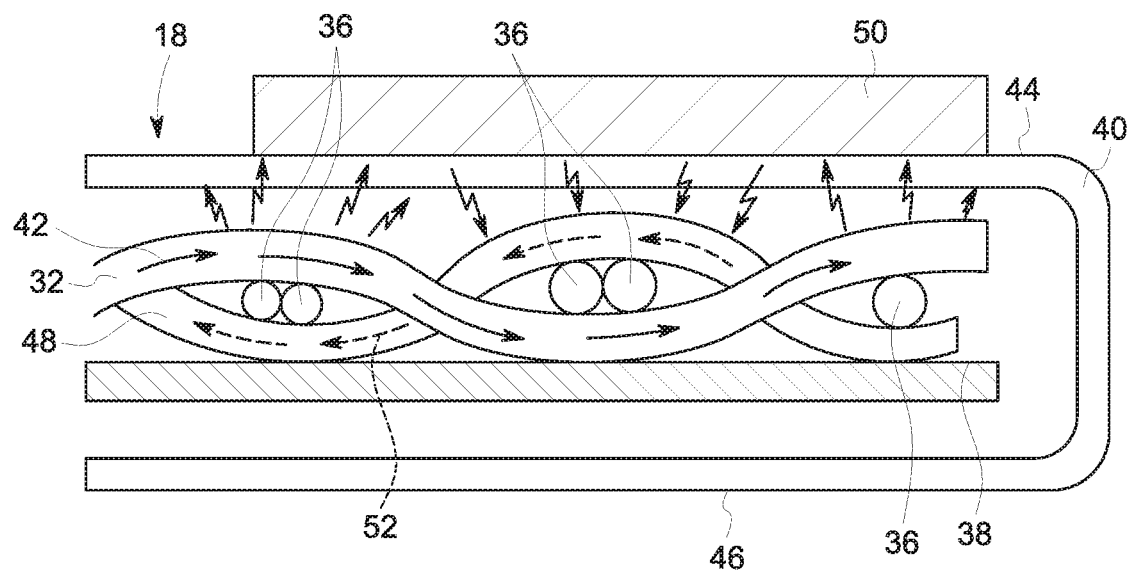
FIG. 3 is a schematic cross-section view of the blanket of FIG. 2 taken along line 3-3 in accordance with an exemplary embodiment.

Referring now to FIG. 3, each of the light emitting optical fibers 32 may be made from one or more optical fiber strands, each strand including a light transmitting core portion of a first transparent material and an outer sheath or cladding of a second transparent material. The sheath material (i.e., the second transparent material) has a lower index of refraction than that of the core material (i.e., the first transparent material) in order to prevent the escape of light. The core material can be made of either glass or plastic or a multi-strand filament having the desired optical characteristics. Because the index of refraction of the sheath material is lower than that of the core material, substantially total reflection is achieved at the sheath-core interface. To cause light to be emitted from the light emitting panel 18, the optical fibers 32 are bent at a plurality of locations along the length. The angle of each bend of the optical fibers 32 approximately exceeds the angle of internal reflection so that a portion of the light can be emitted at each bend. In some embodiments, the optical fibers 32 are woven in the warp direction, with fill threads 36 woven in the weft direction and crossed by the optical fibers 32 to form the bends at the optical fibers 32. The fill threads 36 can be made of conventional fibers, such as cotton, nylon, wool, and the like. In some embodiments, the fill threads 36 are made of a transparent thermoplastic so that they do not interfere with the light transmitted towards the infant. In some embodiments, the fill threads 36 are made of transparent and thermally conductive materials so that they do not interfere with the light or heat transmitted towards the infant.

The light output pattern from the panel 18 can be varied by changing the weave spacing and pattern of the woven optical fibers 32 as well as the shape and radius of the bends at various locations. For example, the illumination can be increased by placing the bends closer together or by making the weave progressively tighter as the distance from the cable 26 increases. Fill threads 36 with different coefficients of friction can be used to help control the tightness of the weave, in that the higher the coefficient of friction, the tighter it is possible to weave the optical fibers 32. In addition, more than one fill threads 36 may be used at the bend to provide more surface points for increased friction, and to reduce the thickness of each individual fill thread 36 and thus the thickness of the light emitting panel 18 while achieving substantially the same rigidity provided by a thicker fill thread. In some embodiments, a reflective layer 38 is disposed adjacent to the light emitting panel 18 to direct the scattered light toward the infant.

In some embodiments, the optical fibers 32 are coated with a material (not shown in the present Figures) that can change the attenuation of the optical fibers 32. The amount of attenuation can be varied by varying the index of refraction and thickness of the applied coating. In some embodiments, the coating is applied to the entire length of the optical fibers 32 so that attenuation changes occur over the entire light emitting portion. In other embodiments, only selected areas of the bends of the optical fibers 32 are coated with the coating to change the attenuation of the light emitted from the selected areas.

In some embodiments, the light emitting panel 18 is at least partly surrounded with a cover 40 as a contamination barrier between the light emitting panel 18 and the skin of the infant. In some embodiments, the cover 40 includes a disposable overwrap made from thin biocompatible polymer, such as polyethylene, polyurethane or cellophane, and is transparent so as not to substantially reduce the intensity of light transmitted to the infant. In some embodiments, the cover 40 is made from thin washable fabric, such as cotton, nylon, or the like. The cover 40 can be loosely fitted over the light emitting panel 18 in any form and can be secured by tape, elastic, or other means, and thus easily removed and disposed of or laundered for sanitary purposes.

As illustrated in FIG. 3, each of the optical fibers 32 receives the treatment light which travels along the length of the optical fibers 32 as illustrated by arrows 42. At each of the bends in the optical fibers 32, light is emitted, as is illustrated by the arrows in FIG. 3. The emitted light is directed through the outer surface 44 of the cover 40. In the embodiment shown, a reflective layer 38 can be positioned beneath the woven optical fibers 32 to cause the treatment light directed toward the outer surface 46 of the cover 40 to be reflected and directed through the outer surface 44. Thus, treatment light is reflected and ultimately delivered to the patient at a level dictated by the weave, the density of the emitting optical fibers 32 that form the weave of the light emitting panel 18 and the location of the reflective layer 38.

As discussed previously, the amount of therapy light delivered through the outer surface 44 was previously measured utilizing an external light meter before the blanket 12 including the light emitting panel 18 is put into use. As the therapeutic blanket 12 is used with patients, it is suggested by the manufacturer that the amount of treatment light being delivered through the inner surface 44 should be measured utilizing an external meter at various intervals of use. However, such measurement requires use of a separate light meter, which often cannot be found or takes additional time. Thus, the amount of treatment light delivered to the infant patient is often not measured at as regular of an interval as desired. This problem was identified by the inventor and the present disclosure developed to address this issue.

As discussed in FIG. 1, the blanket 12 is designed to incorporate and integrate a light receiver 20 that operates to receive a portion of the treatment light delivered by the light emitting panel 18 and return this portion of treatment light to the controller 14 for analysis utilizing the light detector 28. In the embodiment shown in FIG. 3, the light receiver includes a plurality of receiving optical fibers 48 that are interwoven with the emitting optical fibers 32. The receiving optical fibers 48 are not connected to the light source and thus do not receive the treatment light for delivery to the patient. Instead, the receiving optical fibers 48 are designed to receive a portion of the treatment light that is reflected by a reflective element 50 securely attached to a portion of the outer surface 44 of the cover 40. As illustrated in FIG. 3, a portion of the treatment light generated by the light emitting panel 18 contacts the reflective element 50 and is reflected back toward the receiving optical fibers 48 that form part of the woven light emitting panel 18. The light reflected from the reflective element 50 enters into the receiving optical fibers and travels in the direction shown by the broken arrows 52. The receiving optical fibers 48 are brought together and bundled to form the second fiber optic cable 30. The second fiber optic cable 30 can transmit light from the bundled receiving optical fibers 48 back to the light detector 28 included in the housing of the controller 14, as shown in FIG. 1.

In the embodiment shown in FIG. 3, each of the receiving optical fibers 48 can also include a sheet material that has a lower index of refraction than the core material in order to prevent the escape of light once the light is received within the receiving optical fibers 48 at one of the bends.

As can be seen in FIG. 2, the reflective element 50 is positioned over only a very small portion of the entire surface area of the light emitting panel 18. Thus, the reflective element 50 reflects only a very small portion of the treatment light that would otherwise be delivered to the patient. Thus, the reflective element 50 does not affect the overall operation of the light emitting panel 18 in the delivery of the treatment light to the infant patient. The reflective element 50 can be any type of reflective material that can be securely attached to the outer surface 44 of the cover 40. The size and thickness of the reflective element 50 can also be configured depending upon the size of the light emitting panel 18 and the amount of reflected light needed to make an accurate measurement at the controller 14.

The light detector 28 shown in FIG. 1 receives the reflected light from the light receiver 20 through the second fiber optic cable 30. The light detector 28 can then determine the intensity of the light received. Based upon the amount of light received, the phototherapy controller 22 can determine whether or not the light emitting panel 18 is operating in accordance with desired and expected operating parameters. The light detector 28 can be a conventional light detector that generates measurement information based upon the intensity of light received from the light receiver 20 through the cable 30.

Figure 4:
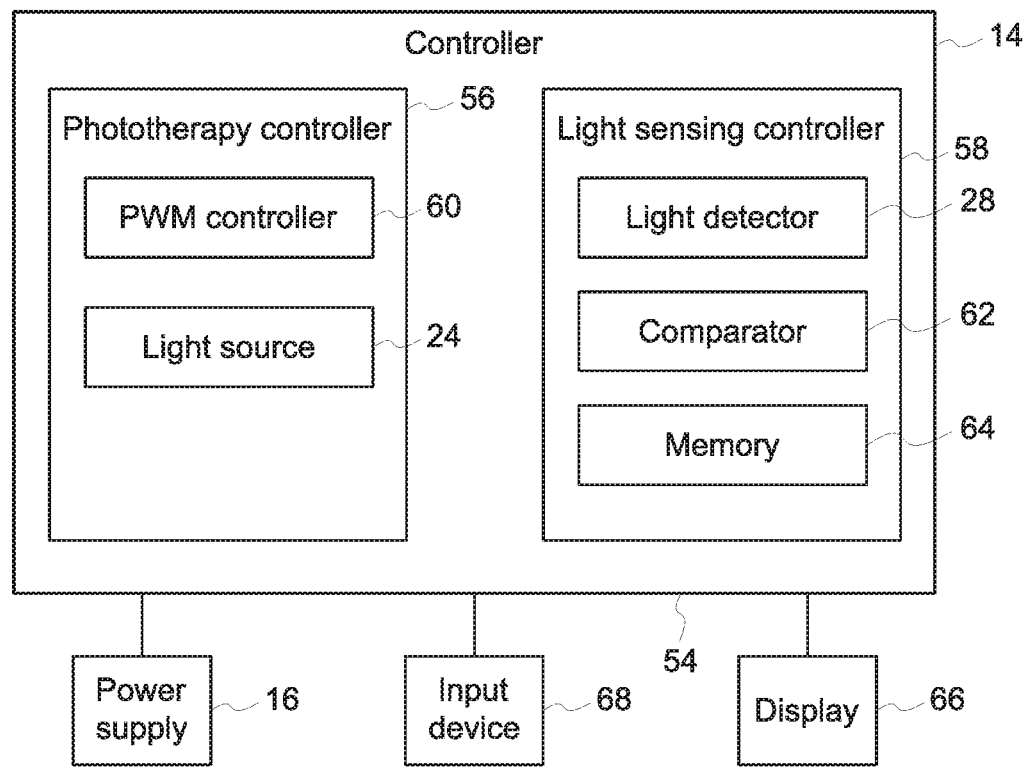
FIG. 4 is a schematic block diagram of a controller that can be used as part of the phototherapy device shown in FIG. 1.

Referring now to FIG. 4, an exemplary block diagram of the controller 14 is shown in accordance with one embodiment of the disclosure. The controller 14 is shown contained within an outer housing 54. The controller 14 generally includes a phototherapy controller 56 and a light sensing controller 58. The phototherapy controller 56 controls the amount of therapy light generated to the blanket while the light sensing controller 58 determines the amount of light received from the integrated light receiver of the blanket.

In some embodiments, the phototherapy controller 56 includes a pulse width modulation (PWM) controller 60 and the blue light source 24. During phototherapy treatment of a patient, the intensity of light delivered to the patient is controlled by the duty cycle of the operation of the light source 24, which is controlled by the PWM controller 60. In order to increase the intensity of therapy light delivered to the patient, the duty cycle of the light source 24 is increased through use of the PWM controller.

The light sensing controller 58 includes the light detector 28 that receives the reflected portion of the therapy light received by the integrated light receiver 20. The light detector 28 converts the intensity of light received into an electric value which is compared to a desired value using the comparator 62 and the memory 64. Based upon this comparison, the light sensing controller 58 can provide an indication to an operator through a user display 66. The user display 66 can indicate to the operator whether the light intensity delivered to the patient meets desired levels. An input device 68 can be used by the operator to control the operation of the phototherapy device 10 either by increasing or decreasing the duty cycle.

Figure 5:
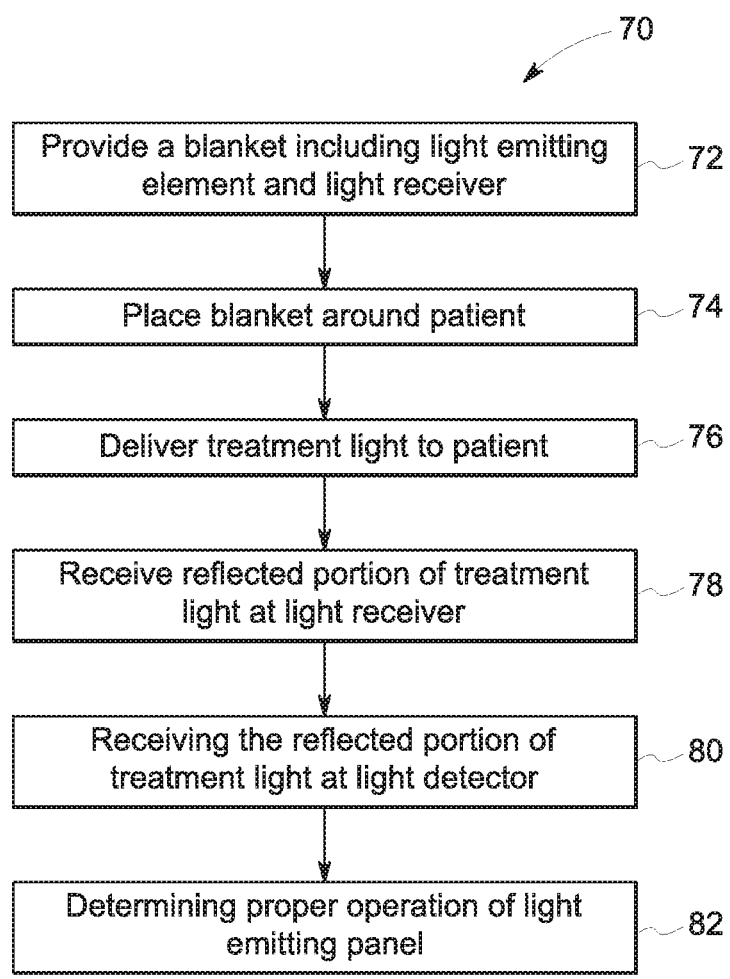
FIG. 5 is a flow char of a method for providing phototherapy treatment by using the phototherapy device of FIG. 1.

Referring now to FIG. 5, a flowchart 70 of a method of providing phototherapy treatment to an infant patient is shown in accordance with one exemplary embodiment of the present disclosure. Initially, a blanket is provided that includes both a light emitting panel and a light receiver that are integrated into the blanket. In some embodiments, the blanket has the same structure as the blanket 12 shown in FIGS. 2-3. In particular, the blanket includes a light emitting panel that is formed from woven light emitting optical fibers. The light receiver integrated into the blanket is formed from a series of receiving optical fibers that are woven together with the emitting optical fibers of the light emitting panel. The emitting optical fibers are designed to transmit treatment light for phototherapy while the receiving optical fibers are designed to receive a portion of the treatment light released by the optical fibers of the light emitting panel. The blanket provided in step 72 is placed around the infant patient as illustrated in step 72. Once the blanket has been placed around the infant patient, treatment light is delivered to the patient as illustrated in step 76. As described previously, treatment light is delivered to the patient by the phototherapy controller 22 controlling the operation of the light source 24 as shown in FIG. 1. The therapy light generated from the light source 24 is provided through the first fiber optic cable 26 to the light emitting panel 18. It is contemplated that phototherapy can be delivered to the infant patient as desired. For example, a clinician may measure the bilirubin level of the infant multiple times a day and set desired phototherapy light intensity based upon the measurement of the bilirubin level of the infant patient. The phototherapy light intensity can be changed by changing the duty cycle of the power provided to the light source. The greater the duty cycle, the higher the intensity of the phototherapy light.

In step 78, the method receives a reflected portion of the treatment light at the light receiver. As discussed previously, a reflective element is placed above a portion of the light emitting panel such that a portion of the treatment light emitted by the light emitting panel is reflected back to the light receiver. In the exemplary embodiment of the disclosure discussed above, the light receiver is formed from a series of receiving optical fibers that are not connected to the light source but are integrated into the woven light emitting panel. The reflected portion of the treatment light received by the light receiver is directed to the light detector contained within the controller 14, as illustrated by step 80. As indicated previously, the light detector 28 contained within the controller housing receives the amount of light contained within the receiving optical fibers and provides an analysis of the intensity and amount of light. In step 82, the phototherapy controller 22 can determine whether the light emitting panel is operating in a proper manner based upon the information provided by the light detector 28. If the amount of treatment light being emitted by the light emitting panel 18 is not at a desired level, the phototherapy controller 22 can provide an indication to the user or can modify the operation of the light source. As can be understood by the above disclosure, integrating the light receiver 20 into the blanket 12 eliminates the need for an external light meter, which solves a problem identified by the inventor during the development of the present disclosure.

Referring now to FIG. 4, an exemplary block diagram of the controller 14 is shown in accordance with one embodiment of the disclosure. The controller 14 is shown contained within an outer housing 54. The controller 14 generally includes a phototherapy controller 56 and a light sensing controller 58. The phototherapy controller 56 controls the amount of therapy light generated to the blanket while the light sensing controller 58 determines the amount of light received from the integrated light receiver of the blanket.

In some embodiments, the phototherapy controller 56 includes a pulse width modulation (PWM) controller 60 and the blue light source 24. During phototherapy treatment of a patient, the intensity of light delivered to the patient is controlled by the duty cycle of the operation of the light source 24, which is controlled by the PWM controller 60. In order to increase the intensity of therapy light delivered to the patient, the duty cycle of the light source 24 is increased through use of the PWM controller.

The light sensing controller 58 includes the light detector 28 that receives the reflected portion of the therapy light received by the integrated light receiver 20. The light detector 28 converts the intensity of light received into an electric value which is compared to a desired value using the comparator 62 and the memory 64. Based upon this comparison, the light sensing controller 58 can provide an indication to an operator through a user display 66. The user display can indicate to the operator that the light intensity delivered to the patient does not meet desired levels. An input device 68 can be used by the operator to control the operation of the phototherapy device 10 either by increasing or decreasing the duty cycle.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for use in phototherapy treatment of a patient, the system comprising:
 a light source configured to generate treatment light used in the phototherapy treatment;
 a blanket coupled to the light source to receive the treatment light and deliver the treatment light to the patient;
 a light receiver integrated into the blanket and operable to receive a portion of the treatment light delivered to the patient;
 a reflective element positioned on the blanket, wherein the portion of the treatment light is reflected toward the light receiver by the reflective element; and
 a light detector coupled to the light receiver and operable to determine an amount of treatment light delivered to the patient by the blanket.

2. The system of claim 1 wherein the blanket includes a light emitting panel made from a plurality of emitting optical fibers woven together, wherein each of the emitting optical fibers receive the treatment light from the light source.

3. The system of claim 2 wherein the light emitting panel further includes fill threads crossed by the emitting optical fibers to form bends at a plurality of locations that emit light for phototherapy.

4. The system of claim 2 wherein the light receiver includes a plurality of receiving optical fibers integrated into the blanket and operable to receive the portion of treatment light.

5. The system of claim 1 further comprising a cover at least partially surrounding the light emitting panel, wherein the reflective element is mounted to the cover.

6. The system of claim 5 further comprising a reflective layer adjacent to the light emitting panel and configured to direct the light emitted from the light emitting panel to the patient.

7. The system of claim 6 wherein the reflective layer is positioned on an opposite side of the emitting panel from the reflective element.

8. The system of claim 1 further comprising a phototherapy controller configured to control the operation of the light source.

9. The system of claim 1 wherein the blanket includes a light emitting panel made from a plurality of woven optical fibers, wherein the light source is coupled to a first portion of the plurality of optical fibers from which a treatment light for phototherapy treatment is emitted, the light receiver includes a second portion of the plurality of optical fibers from which the portion of the treatment light is received.

10. The system of claim 9 wherein the second portion of the plurality of optical fibers are connected to the light detector.

11. A blanket for use in phototherapy treatment of a patient, the blanket comprising:
 a light emitting panel configured to receive treatment light from a light source and deliver the treatment light to the patient when the patient is placed on the blanket;
 a cover at least partially surrounding the light emitting panel, wherein the cover is transparent to the treatment light;
 a light receiver integrated into the blanket and operable to receive a portion of the treatment light delivered to the patient; and
 a reflective element positioned on the cover, wherein the portion of the treatment light is reflected toward the light receiver by the reflective element.

12. The blanket of claim 11 wherein the light receiver includes a plurality of receiving optical fibers integrated into the blanket and operable to receive the portion of treatment light.

13. The blanket of claim 11 further comprising a reflective layer positioned adjacent to the light emitting panel and configured to direct the light emitted from the light emitting panel to the patient.

14. The blanket of claim 13 wherein the reflective layer is positioned on an opposite side of the emitting panel from the reflective element.

15. A method of providing phototherapy treatment to a patient, the method comprising:
 providing a blanket including a light emitting panel and a light receiver;
 delivering a treatment light to the light emitting panel of the blanket such that the light emitting panel emits the treatment light to the patient when the patient is positioned on the blanket;
 positioning a reflective element on the blanket to reflect a portion of the treatment light away from the patient;
 receiving the portion of the emitted treatment light with the light receiver;
 directing the received portion of the emitted treatment light to a light detector; and
 operating the light detector to determine the amount of treatment light emitted by the light emitting panel.

16. The method of claim 15 wherein the light emitting panel is made from a plurality of woven optical fibers, wherein the treatment light is received in a first portion of the plurality of optical fibers from which a treatment light for phototherapy treatment is emitted, wherein the light receiver includes a second portion of the plurality of optical fibers from which the portion of the treatment light is received.

17. The method of claim 15 wherein the light detector determines the amount of light emitted by the light emitting panel as the patient is positioned on the blanket.

* * * * *